United States Patent [19]

Himmelmann et al.

[11] Patent Number: 4,894,324

[45] Date of Patent: Jan. 16, 1990

[54] HARDENERS FOR PROTEINS, A LAYER OF BINDER HARDENED THEREWITH AND A PHOTOGRAPHIC RECORDING MATERIAL CONTAINING SUCH A LAYER

[75] Inventors: Wolfgang Himmelmann; Johannes Sobel, both of Leverkusen; Hans Öhlschläger, Bergisch Gladbach; Karl-Wilhem Schranz, Odenthal-Hahnenberg, all of Fed. Rep. of Germany

[73] Assignee: Agfa-Gevaert Aktiengessellschaft, Leverkusen, Fed. Rep. of Germany

[21] Appl. No.: 163,738

[22] Filed: Mar. 3, 1988

[30] Foreign Application Priority Data

Mar. 17, 1987 [DE] Fed. Rep. of Germany ....... 3708541

[51] Int. Cl.⁴ ................................................ G03C 1/30
[52] U.S. Cl. .................................... 430/622; 430/623; 530/354

[58] Field of Search ............... 430/621, 622, 623, 626; 530/354

[56] References Cited

U.S. PATENT DOCUMENTS

| | | | |
|---|---|---|---|
| 4,039,520 | 8/1977 | Habu et al. | 430/626 |
| 4,323,646 | 4/1982 | Bergthaller et al. | 430/622 |
| 4,338,394 | 7/1982 | Himmelmann et al. | 430/621 |
| 4,349,624 | 9/1982 | Sobel et al. | 430/622 |
| 4,543,324 | 9/1985 | Himmelmann | 430/622 |

FOREIGN PATENT DOCUMENTS 207399 1/1987 European Pat. Off. .

Primary Examiner—Paul R. Michl
Assistant Examiner—Mark R. Buscher
Attorney, Agent, or Firm—Connolly & Hutz

[57] ABSTRACT

Water soluble sulphates of a heteroaromatic bis- or poly-sulphone are suitable for use as hardeners for proteinaceous binders, in particular in photographic layers.

5 Claims, No Drawings

HARDENERS FOR PROTEINS, A LAYER OF BINDER HARDENED THEREWITH AND A PHOTOGRAPHIC RECORDING MATERIAL CONTAINING SUCH A LAYER

The present invention relates to heteroaromatic compounds containing sulphonyl ethyl sulphate groups, with or without vinyl sulphone groups, as hardeners for proteins, hardened binder layers in which the binder contains a protein, and in particular a light sensitive photographic recording material whose proteinaceous binder layers are hardened with the hardeners according to the invention.

Numerous substances have been described as hardeners for proteins, in particular for gelatine. These include, for example, metal salts such as chromium, aluminium or zirconium salts, aldehydes and halogenated aldehyde compounds, in particular formaldehyde, dialdehydes and mucochloric acid, 1,2- and 1,4-diketones such as cyclohexane-1,2-dione and quinones and chlorides or anhydrides of poly basic organic acids, such as anhydrides of tetracarboxylic acids, compounds containing several reactive vinyl groups, such as vinyl sulphones or acrylamides, compounds containing at least two heterocyclic, 3 membered rings which are easily opened, such as ethylene oxide and ethylene imine, poly functional methane sulphonic acid esters and bis-α-chloracyl amido compounds.

High molecular weight hardeners such as polyacrolein and its derivatives or copolymers and alginic acids derivatives have recently become known, especially for use as hardeners which are confined to a layer.

The use of the above mentioned compounds for photographic purposes, however, has numerous serious disadvantages. Some of these compounds are photographically active and therefore unsuitable for hardening photographic recording materials while others have such an adverse effect on the physical properties, e.g. the friability of the gelatine layers, that they are unusable for this reason. Others again give rise to discolourations or a change in the pH during the hardening reaction. Furthermore, it is particularly important for the hardening of the photographic layers that it should reach a maximum as rapidly as possible after drying so that the permeability of the hardening material to the developer solution will not continuously change, as is the case when mucochloric acid or formaldehyde is used as hardener.

Some crosslinking agents for gelatine, such as ethylene imine compounds, may have a damaging effect on the skin and are therefore unsuitable on physiological grounds.

It is also known to use trichlorotriazine, hydroxydichlorotriazine and dichloroaminotriazines as hardeners. The disadvantages of these hardeners lie in their relatively high vapour pressure, their release of hydrochloric acid during hardening and their physiological effects. Water soluble derivatives which contain carboxylic and sulphonic acid groups and which have been obtained by the reaction of cyanuric chloride with one mol of a diaminoalkyl or diaminoaryl sulphonic acid or carboxylic acid do not show these disadvantages and have therefore recently been proposed as hardeners. Their practical usefulness is, however, limited as they decompose when left to stand in aqueous solutions owing to their high solubility and therefore rapidly lose their effect.

For a hardener used for photographic layers containing gelatine it is of the utmost importance, both for reasons of preparation and for reasons of processing, that the onset of the crosslinking reaction should be predeterminable within certain limits, for example by suitable choice of the drying temperature or the pH.

Compounds containing two or more acrylamide groups in the molecule, such as N,N',N"-tris-acryloyl-hexahydrotriazine or methylene-bis-acrylamide, are also known as hardeners for photographic gelatine layers.

Although these compounds still have a satisfactory hardening action after some time, they are difficult to dissolve in water and therefore may not bring about uniform hardening throughout the layer.

The rapid processing of photographic recording materials, in particular colour photographic materials, which is increasingly employed nowadays, gives rise to special problems as it makes increased demands on the mechanical properties and the swelling characteristics of the recording materials. Added to this are the difficulties which arise from the necessity to produce ever thinner photographic layers. It has been attempted to solve such problems by using different types of hardeners. The known hardeners have either caused fresh difficulties or simply proved to be unsuitable. These hardeners include the numerous known hardeners containing vinyl sulphone groups, among which divinyl sulphone (DE-C 872 153) is one of the earliest known hardeners of this type. One disadvantage of divinyl sulphone is its toxicity.

Aromatic vinyl sulphone compounds have been disclosed in DE-C-1 100 942, and vinyl sulphonyl alkyl compounds, including those containing a heterocyclic ring, have been disclosed in DE-A-1 547 733, DE-B2-1 808 685 and DE-A-2 348 194.

The known vinyl sulphone compounds have proved to be disadvantageous as hardeners in several respects. They are either insufficiently water soluble and necessitate special measures to enable them to be used in photographic gelatine layers or they have a deleterious effect on the drying properties of the layers. Others of these compounds, again, increase the viscosity of the casting compositions to such an extent that it becomes difficult to work these compositions up into layers. Furthermore, known hardeners of the vinyl sulphone type cause the migration of photographic additives from one layer to another, especially in colour photographic recording materials, thereby giving rise to colour changes and changes in the photographic properties.

Lastly, reaction products obtained from the reactions of compounds containing at least 3 vinyl sulphonyl groups in the molecule with compounds containing a water soluble group and a group capable of reacting with a vinyl sulphonyl group are disclosed as hardeners in DE-A-2 635 518. These reactions may give rise, for example, to anionic vinyl sulphonyl compounds.

These compounds do, however, have disadvantages. They are found to undergo considerable after-hardening in photographic layers containing gelatine, i.e. their optimum effect sets in only after the material has been in storage for some time. As a result, swelling of the layer in water decreases with increasing length of storage so that the sensitometric data of the material continuously change. Moreover, if the known compounds have been added to silver halide emulsions containing gelatine, the viscosity increases with increasing digestion time, especially at pH values around 7, so that the emulsions can no longer be satisfactorily cast.

It is also known that the speed of crosslinking of gelatine is particularly high when vinyl sulphonyl compounds of heteroaromatic compounds are added, compared with the speed of crosslinking obtained with other, hitherto known vinyl sulphones. It is a disadvantage that the heteroaromatic bis- and poly-vinyl sulphone compounds are less soluble in water and precipitate when used in aqueous casting solutions. Hardening therefore becomes irregular and in the worst cases leads to reticulation in the layer.

It is an object of the present invention to prepare readily water soluble hardeners for proteinaceous binders, in particular hydrophilic binders, especially gelatine, from heteroaromatic bis- and poly-vinyl sulphone compounds, which hardeners should have the same hardening activity as the starting compounds and should not cause greater after-hardening in photographic layers under normal atmospheric conditions on account of their solubility in water.

The known water soluble addition products of tertiary amines and heteroaromatic bis- or poly-vinyl sulphones have the disadvantage of reacting with the anionic wetting agents which are predominantly used in photographic layers to form water insoluble salts which lead to faults in casting.

The present invention therefore relates to water soluble heteroaromatic compounds containing sulphonyl ethyl groups, with or without vinyl sulphone groups, by means of which the above mentioned problem may be solved.

The invention further relates to hardened binder layers in which the binder contains a protein, in particular a hydrophilic protein, preferably gelatine, which is hardened with the hardeners according to the invention.

The present invention also relates to a light sensitive photographic recording material having at least one gelatine-containing layer hardened with a hardener, characterized in that a hardener according to the present invention is used for hardening.

The hardeners used according to the invention preferably correspond to the following general formula (I):

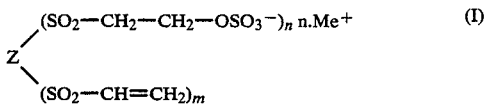

wherein
Z denotes an optionally substituted heteroaromatic ring containing at least n+m ring carbon atoms and at least one ring O, S or N atom,
Me denotes a metal cation such as Li+, Na+ or K+,
n denotes an integer>0,
m denotes an integer≧0 and
m+n represent an integer≧2, preferably with a value from 2 to 5.

Heteroaromatic rings are understood to be unsaturated, at the most 5- or 6-membered rings, containing heteroatoms and resembling benzene in containing a π-electronsextet (see H. BEYER, Lehrbuch der organischen Chemie, 18th Edition, (1976), page 613). The heteroaromatic ring denoted by Z may be, for example, a triazole, thiadiazole, oxadiazole, pyridine, pyrrole, quinoxaline, thiophene, furan, pyrimidine or triazine ring. In addition to the at least two vinyl sulphonyl groups, it may contain further substituents and optionally condensed benzene rings which may in turn be substituted. The following are examples of heteroaromatic rings (Z):

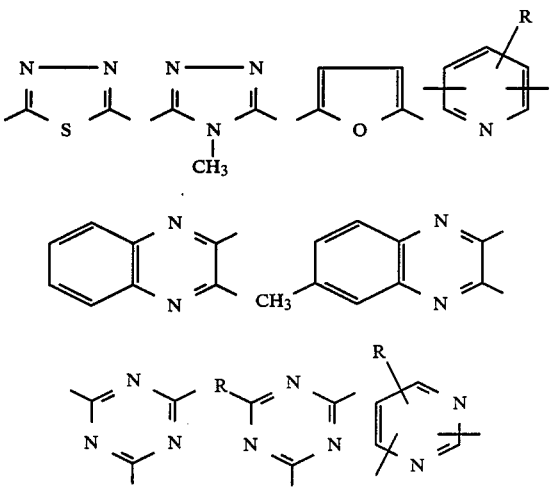

wherein R denotes $C_1$–$C_4$ alkyl, phenyl or $C_1$–$C_4$ alkoxy. Z preferably denotes a 1,2,4-thiadiazole or -triazole group.

Compounds of aliphatic or non-aromatic heterocyclic bis- or poly-vinyl sulphones containing sulphonyl ethyl sulphate groups are known but it is one of the characteristics of these compounds that they decompose slowly in the photographic layer and only then harden. Severe after hardening is therefore observed, i.e. the maximum of the crosslinking effect is obtained only after days or weeks. This is undesirable for the preparation of photographic materials since they should if possible be sold without previous prolonged storage. Moreover, the photographic properties of the material continually change as hardening progresses.

It is surprising to find that, in contrast to the previously known compounds, the compounds of heterocyclic aromatic compounds containing sulphonyl ethyl sulphate groups according to the present invention react exceptionally rapidly with amino group-containing compounds such as gelatine to undergo crosslinking. Although they are highly active, their aqueous solutions are very stable. Aqueous solutions at concentrations of from 30 to 50% by weight may be kept for several months at room temperature without any polymerisation or change in their activity being observed.

The hardeners according to the invention are obtained from the heterocyclic aromatic compounds containing hydroxyethyl sulphone groups by a reaction with chlorosulphonic acid. The hydroxyethyl sulphone compounds are obtained from the hydroxyethyl thio compounds by the conventional method of oxidation with hydrogen peroxide.

The following compounds are given as examples:

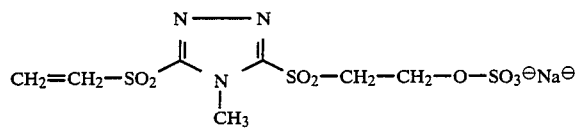 H1

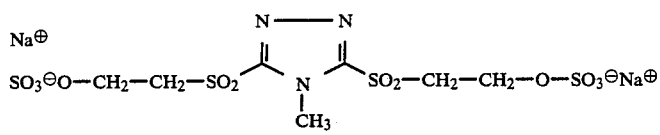 H2

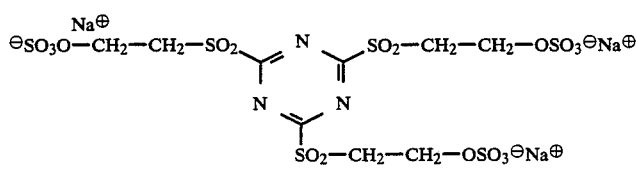 H3

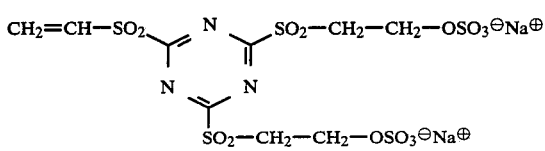 H4

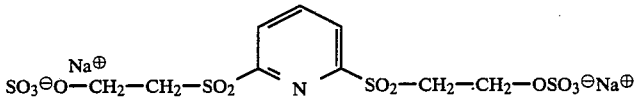 H5

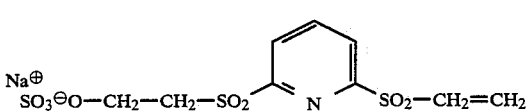 H6

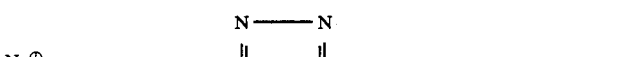 H7

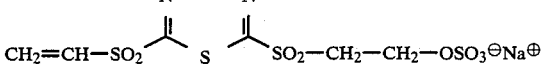 H8

The compounds are prepared from the hydroxy ethyl sulphonyl compounds.

EXAMPLE OF PREPARATION 6 g of 1-N-methyl-2,5-bis-hydroxy ethyl-sulphonyl-1,3,4-triazole are stirred up in 30 ml of absolute dioxane. 9.32 g of chlorosulphonic acid are added dropwise at 10° C. with cooling. The clear, yellowish solution obtained is stirred for three hours at room temperature and then left to stand overnight at room temperature.

The mixture is then precipitated with toluene. The product is triturated several times with fresh toluene. It is then dissolved in ice water and the pH is adjusted to 5 with sodium bicarbonate solution. The toluene adhering to the product is separated off in a separating funnel and the cloudy solution is treated with Fullers earth. A clear, colourless solution is obtained. Yield: 150 g of a 6.6% by weight solution.

The compound is now free from starting material. Analysis shows the compound to correspond to the following formula:

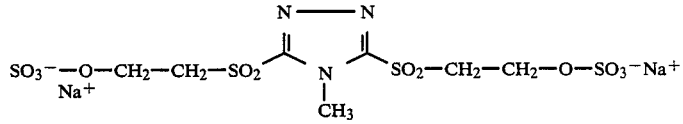

The compounds to be used according to the invention are generally readily soluble in water or a mixture of water and organic solvents.

The hardeners used according to the invention may be added to the casting solution of a binder layer to be produced, e.g. a photographic layer, either some time before or immediately before casting, preferably with the aid of suitable dosing apparatus. The compounds may also be added to a top casting solution which is applied as hardening layer over the layer of binder proper after the latter has been prepared. Alternatively, the finished combination of layers may be passed through a solution of the hardener, thereby receiving the necessary quantity of hardener. Furthermore, in multilayered arrangements, e.g. in colour films and colour photographic paper, the crosslinking agents according to the invention may be introduced into the whole arrangement by means of interlayers.

The hardeners according to the invention are generally used in a quantity of from 0.01 to 15% by weight, preferably from 0.1 to 5% by weight, based on the dry weight of the protein in the coating solution, the protein being preferably gelatine. The stage at which the hardener is added to the coating solution is not critical, but silver halide emulsions are preferably added to the hardener after chemical ripening. Compounds which control the pH, such as bicarbonate or sodium acetate, may be applied together with the hardeners according to the invention.

The hardeners according to the invention may be used singly or as mixtures of two or more of the compounds according to the invention or they may be used together with other, known hardeners. The following are examples of suitable additional hardeners: formaldehyde, glutaraldehyde and similar aldehyde compounds, diacetyl, cyclopentadione and similar ketone compounds, bis-(2-chloroethyl urea), 2-hydroxy-4,6-dichloro-1,3,5-triazine and other compounds containing reactive halogen as described in U.S. Pat. Nos. 3,288,775, 2,732,303, GB-A-974 723 and GB-A-1 167 207; divinyl sulphone, 5-acetyl-1,3-diacryloyl-hexahydro-1,3,5,-triazine and other compounds containing a reactive olefine bond, as described in U.S. Pat. Nos. 3,635,718, 3,232,763 and GB-A-994 869; N-hydroxy methyl-phthalimide and other N-methylol compounds as described in U.S. Pat. Nos. 2,732,316 and 2,586,168; isocyanates as described in U.S. Pat. No. 3,103,437; aziridine compounds as described in U.S. Pat. Nos. 3,017,280 and 2,983,611; acid derivatives as described in U.S. Pat. Nos. 2,725,294 and 2,725,295; compounds of the carbodiimide type, as described in U.S. Pat. No. 3,100,704; carbomoyl pyridinium salts as described in DE-A-22 25 230 and DE-A-24 39 551; carbamoyl oxypyridinium compounds as described in DE-A-2 408 814; compounds containing a phosphorous-halogen bond as described in JP-A-113 929/83, N-carbonyl-oximide compounds as described in JP-A-43353/81; N-sulphonyl oxy-imido compounds as described in U.S. Pat. No. 4,111,926, dihydroquinoline compounds as described in U.S. Pat. No. 4,013 468, 2-sulphonyl-oxy pyridinium salts as described in JP-A-110 762/81, formamidinium salts as described in EP-A-0 162 308, compounds containing two or more N-acyloxy-imino groups in the molecule as described in U.S. Pat. No. 4,052,373; epoxy compounds as described in U.S. Pat. No. 3,091,537; compounds of the isoxazole type as described in U.S. Pat. Nos. 3,321,313 and 3,543,292; halogenated carboxy aldehydes, such as mucochloric acid; dioxane derivatives such as dihydroxy dioxane and dichloro dioxane; and inorganic hardeners such as chrome alum and zirconium sulphate. In addition to the above mentioned hardeners, the hardeners according to the invention may also be used together with preliminary stages of the compounds described above, such as adducts of alkali metal bisulphites and aldehydes, methylol derivatives of hydantoin and primary fatty nitro alcohols, etc. When the hardeners according to the invention are used together with other hardeners, the quantity of hardeners according to the invention may be chosen according to requirement, depending on the object to be achieved and the effect to be produced.

The protein in the hardened layer of binder according to the present invention generally serves as binder for the reactive or unreactive substances dispersed therein, such as the dyes or compounds which undergo a change, for example in response to exposure or a subsequent photographic process, and develop a certain activity as a result. Layers of binder which have been hardened according to the invention may be present, for example, in the form of coloured coatings. The hardened protein according to the invention is also suitable for use as binder for diagnostic purposes. Thus, for example, dry chemical testing agents, also known as test strips, may be equipped with a protein layer which has been hardened according to the invention and which contains the reagents required for the specific test reaction, such as enzymes, coenzymes, colour forming compounds and the like. The hardened protein may also be used in photographic or photothermographic single layered or multilayered recording materials, e.g. as binders for silver halide, colour couplers and other photographically active substances.

The term "photographic layers" is used in this context to denote any layers in general which are used in photographic recording materials, e.g. light sensitive silver halide emulsion layers, protective layers, filter layers, antihalation layers, backing layers, image receptor layers or photographic auxiliary layers in general.

The light sensitive gelatine-containing emulsion layers for which the hardeners according to the invention are particularly suitable include, for example, layers containing light sensitive substances, in particular silver halide, optionally in a spectrally sensitized form. Layers of this type are normally present in photographic recording materials for a wide variety of black and white or colour photographic processes, such as negative, positive or diffusion transfer or printing processes. The hardeners according to this invention have proved to be particularly advantageous for hardening photographic layer packs used for carrying out colour photographic processes, e.g. those containing colour couplers or other colour producing compounds or those intended for treatment with solutions containing colour couplers.

The action of the hardeners according to this invention is not impaired by conventional photographic additives and the hardeners are also inert towards photographically active substances such as water soluble or emulsified, water insoluble colour components, stabilizers, sensitizers and the like. Moreover, the hardeners have no deleterious effect on the light sensitive silver halide emulsion.

The light sensitive silver halide in the light sensitive component may be a chloride, bromide or iodide or mixtures thereof. For example, the halide component of at least one layer may consist of from 0 to 12 mol % of iodide, from 0 to 50 mol % of chloride and from 50 to 100 mol % of bromide. The halides may be present predominantly in the form of compact crystals which may be, for example, cubic or octahedral or transitional forms. They mainly have a thickness of more than 0.2 $\mu$m. The average ratio of diameter to thickness is preferably less than 8:1, the diameter of a grain being defined as the diameter of a circle enclosing the same area as the projected surface of the grain. The layers may also contain tabular silver halide crystals in which the ratio of diameter to thickness is greater than 8:1; see in this connection Research Disclosure 22 534 (January 1983). The emulsions may be heterodisperse or monodisperse and preferably have an average grain size of from 0.3 μm to 1.2 μm. The silver halide grains may have a layered grain structure. The emulsions may contain organic silver salts in addition to the silver halide, e.g. they may contain silver benzo-triazolate or silver behenate.

The emulsions may be chemically and/or spectrally sensitized in the conventional manner; they may also be stabilized with suitable additives. Suitable chemical sensitizers, spectral sensitizing dyes and stabilizers have been described, for example, in Research Disclosure 17643; see in particular Chapters III, IV and VI.

The binder mainly used according to this invention is a proteinaceous binder, in particular gelatine. An essential feature of this binder is the presence of functional groups with which the vinyl sulphonyl groups of the hardener according to the invention can react, in particular amino groups. The proteinaceous binder may be partially modified, e.g. by partial acylation, or it may be replaced by other natural or synthetic binders, so long as sufficient reactivity with the hardener according to the invention is maintained. Casting auxiliaries and softeners may also be used; see Research Disclosure 17 643, in particular Chapters IX, XI and XII.

The binder layer may contain photographically inert particles of an inorganic or organic nature, for example, as matting agents or as so called spacers. Such particles may consist of an organic polymer; see, for example, DE-A-33 31 542, DE-A-34 24 893 and Research Disclosure 17 643, Chapter XVI.

Wetting agents, preferably anionic wetting agents, are added to the layers to improve casting. These wetting layers are surface active compounds containing $SO_3^-$, $OSO_3^-$ and $COO^-$ groups. The compounds used may be alkyl sulphonates

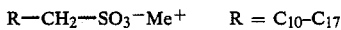

$R—CH_2—SO_3^-Me^+$    $R = C_{10}-C_{17}$

Alkylsulphates

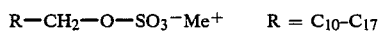

$R—CH_2—O—SO_3^-Me^+$    $R = C_{10}-C_{17}$

Succinic acid ester sulphonates

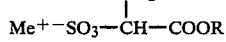

$$\begin{array}{l} \phantom{Me^+-SO_3-}CH_2—COOR \\ Me^+-SO_3—CH—COOR \end{array} \quad R = C_5-C_{10}$$

Alkyl methyl taurine, mono- and dialkyl-naphthalene sulphonates or perfluoro alkyl sulphantes.

The cations used may be, for example, $Li^+$, $Na^+$ or $K^+$.

These may be used in combination with non-ionic or amphoteric wetting agents.

Colour photographic recording materials usually contain at least 1 silver halide emulsion layer for the recording of light of each of the three spectral regions, red, green and blue. For this purpose, the light sensitive layers are spectrally sensitized in known manner by means of suitable sensitizing dyes. Blue sensitive silver halide emulsion layers need not necessarily contain a spectral sensitizer since the intrinsic sensitivity of the silver halide is in many cases sufficient for the recording of blue light.

Each of the above mentioned light sensitive layers may consist of a single layer or it may comprise two or more silver halide emulsion partial layers in known manner, e.g. as in the so called doubled layered arrangement (DE-C-1 121470). Red sensitive silver halide emulsion layers are generally arranged closer to the layer support than green sensitive silver halide emulsion layers which in turn are arranged closer to the support than blue sensitive layers, and a light insensitive yellow filter layer is generally arranged between the green sensitive layers and the blue-sensitive layers, but other arrangements are also possible. A light-insensitive interlayer is generally arranged between the layers of differing spectral sensitivities, and such an interlayer may contain agents for preventing accidental diffusion of developer oxidation products. When a photographic material contains several silver halide emulsion layers of the same spectral sensitivity, these may be arranged directly adjacent to one another or they may be separated by a light sensitive layer of a different spectral sensitivity (DE-A-1 958 709, DE-A-2 530 645, DE-A-2 622 922).

Colour photographic recording materials for the production of multi-colour images generally contain colour producing compounds, e.g. colour couplers in spatial and spectral association with the silver halide emulsion layers of differing spectral sensitivities, for producing the different partial colour images in cyan, magenta and yellow.

By "spatial association" is meant that the colour coupler is so related to the silver halide emulsion layer in its position in space that the two are capable of interacting to produce an imagewise correspondence between the silver image formed in the process of development and the colour image produced from the colour coupler. This is generally achieved by arranging the colour coupler in the silver halide emulsion layer itself or in an adjacent, optionally light insensitive layer of binder.

By "spectral association" is meant that the spectral sensitivity of each of the light sensitive silver halide emulsion layers and the colour of the partial colour image produced from the corresponding, spatially associated colour coupler stand in a certain relationship to one another, each of the spectral sensitivities (red, green, blue) having a different colour of the corresponding partial colour image associated therewith (generally, for example, the colours cyan, magenta and yellow, in that order).

Each of the silver halide emulsion layers which differ from one another in their spectral sensitization may have one or more colour couplers associated therewith. When several silver halide emulsion layers of the same spectral sensitivity are present, each of these layers may contain a colour coupler, and these various colour couplers need not necessarily be identical, provided only that on colour development they give rise at least to approximately the same colour, normally a colour which is complementary to the colour of the light to which the corresponding silver halide emulsion layers are predominantly sensitive.

In preferred embodiments, therefore, red sensitive silver halide emulsion layers have at least one non-diffusible colour coupler associated with them to produce the cyan partial colour image, generally a coupler of the phenol or α-naphthol series. Green sensitive silver halide emulsion layers have at least one non-diffusible colour coupler associated with them for producing the magenta partial colour image, the colour coupler being generally of the 5-pyrazolone, indazolone or pyrazoloazole series. Lastly, blue sensitive silver halide emulsion layers have at least one non-diffusible colour coupler associated with them for producing the yellow partial colour image, generally a colour coupler containing an open chain ketomethylene group. Colour couplers of this type are known in large numbers and have been described in numerous Patent specifications.

Reference may be had, for example, to the publications "Farbkuppler" by W. PELZ in "Mitteilungen aus den Forschungslaboratorien der Agfa, Leverkusen/-Munchen", Volume III, Page 111 (1961) and to the publication by K. VENKATARAMAN in "The Chemistry of Synthetic Dyes", Volume 4, 341 to 387, Academic Press (1971), and to Research Disclosure 17 643, Chapter VIII.

The colour couplers may be either conventional 4-equivalent couplers or they may be 2-equivalent couplers which require less silver halide for the production of colour. 2-equivalent couplers are derived, as is known, from 4-equivalent couplers in that they contain, in the coupling position, a substituent which is split off in the coupling reaction. 2-equivalent couplers include both those which are virtually colourless and those which have an intense colour of their own which disappears in the process of colour coupling to be replaced by the colour of the image dye produced. The latter couplers may be present in addition in the light sensitive silver halide emulsion layers, where they serve as masking couplers to compensate for the unwanted side densities of image dyes. Also to be included among the 2-equivalent couplers are the known white couplers, which do not give rise to a dye when they react with colour developer oxidation products. 2-equivalent couplers also include those couplers which carry, in their coupling position, a releasable group which is released in the reaction with colour developer oxidation products and then develops a particular photographic activity, e.g. as development inhibitor or accelerator, either directly or after it has itself given up one or more groups (e.g. DE-A-27 03 145, DE-A-28 55 697, DE-A-31 05 026, DE-A-33 19 428). The known DIR couplers as well as the DAR and FAR couplers are examples of such 2-equivalent couplers. The group which is released may be a ballast group so that the reaction with colour developer oxidation products gives rise to coupling products, e.g. dyes, which are diffusible or at least have a slight or limited mobility.

By "slight or limited mobility" is meant a mobility of such an extent that the contours of the discrete dye patches formed in the process of chromogenic development merge with one another. This extent of mobility should be distinguished on the one hand from the usual complete immobility in photographic layers, which is the desirable state for colour couplers or for dyes produced from them in conventional photographic recording materials in order that a very sharp image may be obtained, and on the other hand from the full mobility which is required of dyes used, for example, in dye diffusion processes. The last mentioned dyes in most cases have at least one group which renders them soluble in alkaline media. The extent of this slight mobility according to the invention may be controlled by varying the substituents, for example in order to obtain the required degree of solubility in the organic medium of the oil former or the affinity to the binder matrix.

High molecular weight colour couplers are described, for example, in DE-C-1 297 417, DE-A-24 07 569, DE-A-31 48 125, DE-A-32 17 200, DE-A-33 20 079, DE-A-33 24 932, DE-A-33 31 743, DE-A-33 40 376, EP-A-27 284, and U.S. Pat. No. 4,080,211. High molecular weight colour couplers are generally prepared by the polymerisation of ethylenically unsaturated monomeric colour couplers but they may also be obtained by polyaddition of polycondensation.

The binder layers may contain filter dyes and antihalation dyes, e.g. oxonoledyes as described, for example, in U.S. Pat. Nos. 2,274,782, 2,611,696, FR-A-1 290 430, GB-A-1 177 429, DE-A-1 572 256, DE-A-22 59 746, DE-A-23 21 470, U.S. Pat. No. 3,984,246; styryl dyes as described, for example, in U.S. Pat. No. 2,036,546, DE-B-1 014 430, DE-B-1 028 425, DE-B-1 112 801 and DE-B-1 104 335; azo dyes as described in DE-B-1 103 135, DE-B-1 182 067, GB-A-1 122 298 and DE-A-1 547 646; triphenyl methane dyes as described in DE-B-1 008 114; anthraquinone dyes as described in U.S. Pat. No. 2,865,752; or merocyanines as described in GB-A-1 030 392 or in U.S. Pat. No. 4,366,221. See also Research Disclosure 17 643, Chapter VIII.

The binder layers may contain UV-absorbants optionally in a high molecular weight form; see DE-A-35 01 722, DE-A-35 05 423, DE-A-35 31 383, EP-A-0 027 242, EP-A-0 057 160 and Research Disclosure 17 643, Chapter VIII, and Research Disclosure 18 716, in particular Page 650, left hand column.

The binder layers may contain dye stabilizers as described in DE-A-35 01 722, EP-A-0 011 051, EP-A-0 026 742, EP-A-0 069 070, EP-A-0 098 241, EP-A-0 114 028, EP-A-0 114 029 and Research Disclosure 17 643, Chapter VII, in particular Section J.

The binder layers may contain optical brightening agents or white toners; see, for example, Research Disclosure 17 643, Chapter V.

The binder layers may contain so called scavenger compounds, i.e. compounds which are capable of reacting with developer oxidation products and of preventing their diffusion into adjacent layers; see, for example, EP-A-0 098 072, EP-A-0 124 877, EP-A-0 069 070, U.S. Pat. No. 4,366,226 and EP-A-0 125 522 and Research Disclosure 17 643, in particular Chapter VII, Section I, as well as Research Disclosure 17 842 (February 1979) and Research Disclosure 18 716 (November, 1979), in particular Page 650.

The compounds which are to be introduced may be added by first preparing a solution or dispersion of the particular compound and then adding this to the casting solution. The choice of solvent or dispersing agent varies according to requirement. Hydrophobic compounds may be introduced into the casting solution by means of high boiling solvents, so called oil formers. Suitable methods are described, for example, in U.S. Pat. No. 2,322,027, DE-A-1 722 192 and EP-A-0 043 037. The compounds may also be introduced into the casting solution in the form of charged latices; see, for example, DE-A-25 41 230, DE-A-25 41 274, DE-A-28 35 856, EP-A-0 014 921, EP-A-0 069 671, EP-A-0 130 115, and U.S. Pat. No. 4,291,113.

The binder layers may also contain agents which are capable of reacting with aldehydes, in particular with formaldehyde, namely so called aldehyde removers or compounds which are capable of protecting other compounds incorporated in the layers, in particular other colour couplers against the harmful effect of aldehydes. Examples of such aldehyde removers include N,N'-ethylene urea, 2,3-dihydroxy naphthalene and dimedon; see, for example, DE-A-1 772 816.

The recording material according to this invention is worked up by developing it with a colour developer compound. The colour developer compounds used may be any developer compounds which are capable of reacting in the form of their oxidation product with color couplers to form azomethine or indoquinone dyes. Suitable colour developer compounds include aromatic compounds of the p-phenylene diamine series containing at least one primary amino group, e.g. N,N-dialkyl-p-phenylene diamines, such as N,N-diethyl-p-phenylene diamine, 1-(N-ethyl-N-methylsulphonamidoethyl)-3-methyl-p-phenylene diamine, 1-(N-ethyl-N-hydroxyethyl-3-methyl-p-phenylene diamine and 1-(N-ethyl-N-methoxy ethyl)-3-methyl-p-phenylene diamine. Other suitable colour developers are described, for example, in J. American Chem. Soc. 73, 3106 (1951) and in G. Haist, Modern Photographic Processing, 1979, John Wiley and Sons, New York, Page 545 etc.

After colour development, the material is bleached and fixed in the usual manner. Bleaching and fixing may be carried out separately or together. The usual compounds may be used as bleaching agents, e.g. $Fe^{3+}$ salts and $Fe^{3+}$ complex salts such as ferricyanides, dichromates, water soluble cobalt complexes, etc. Iron-III complexes of aminopolycarboxylic acids are particularly preferred, in particular, for example, ethylenediaminotetracetic acid, nitrilotriocetic acid, iminodiacetic acid, N-hydroxyethylethylene diaminotriacetic acid, alkyl imino dicarboxylic acids and corresponding phosphonic acids. Persulphates are also suitable bleaching agents.

Advantageous results may be obtained by using an aqueous final bath containing little or no formaldehyde.

EXAMPLE 1

The following layers were applied successively to a cellulose triacetate layer support covered with an adhesive layer (the quantities given are based on 1 m²).
1. An antihalation layer containing 4 g of gelatine and 0.7 g of colloidal black silver,
2. A red sensitive layer 6 μm in thickness containing 35 mmol of silver iodo-bromide (5 mol % AgI), 4 mmol of a cyan coupler corresponding to the formula

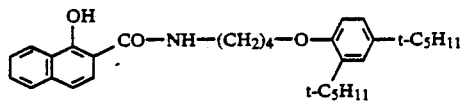

6 g of gelatine and 0.3 g of dibutylnaphthalene sulphonic acid sodium,
3. A gelatine interlayer 0.5 μm in thickness,
4. A green sensitive layer 6 μm in thickness containing 30 mmol of silver iodo-bromide (5 mol % AgI), 1.3 mmol of a magenta coupler corresponding to the formula,

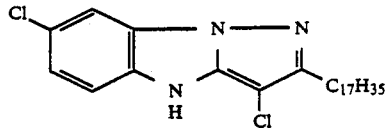

5 g of gelatine and 0.2 g of dibutylnaphthalene sulphonic acid sodium,
5. a gelatine interlayer 0.5 μm in thickness,
6. a yellow filter layer containing 1.5 g of gelatine and 0.2 g of colloidal yellow silver,
7. a blue sensitive layer 6 μm in thickness containing 13 mmol of silver-iodo bromide (5 mol % AgI), 2 mmol of a yellow coupler corresponding to the formula

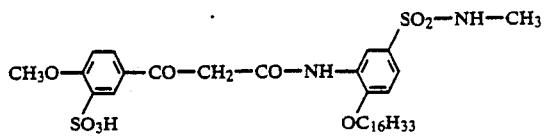

and 5 g of gelatine, and
8. a gelatine layer 1 μm in thickness.

All the casting solutions contained sulphosuccinic acid octyl ester in the form of its sodium salt as wetting agent for casting.

The combination of layers was then dried.

The photographic film thus obtained was used in the following experiments as comparison material.

Preparation of this film was repeated but in each film sample one of the hardeners H-2 or H-3 or, for comparison, the hardener V-1 which was not according to the invention was added to individual layers in a quantity of 0.0075 mol/100 g of gelatine.

The hardener V-1 which was not according to the invention corresponded to the formula

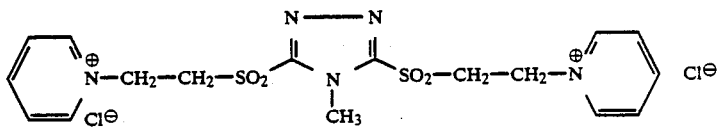

After the samples had been hardened as described, they were tested by the methods described below. The results are entered in Table 1.

The hardening achieved in the photographic layers was determined by means of the melting point of the layers, which may be measured as described below.

The combination of layers cast on a support is half dipped in water which is continuously heated to 100° C. The temperature at which the layer runs off the support (formation of streaks) is taken as the melting point or the melting off point. When this method of measuring is used, unhardened protein layers or colour layers in no case show an elevation in melting point. Under these conditions, the melting off point is in the region of from 30° to 35° C.

To determine the water absorption, the test sample was developed as a black sheet in a conventional colour development process and after the sample had been removed from the final bath and excess water had been stripped off, the sample was weighed. It was then dried and reweighed. The weight difference converted from the surface area of the sample to 1 m² gives the water absorption per m².

Swelling was determined gravimetrically after 10 minutes' treatment of a sample strip in distilled water at 22° C. It is defined by the swelling factor as follows:

$$\frac{\text{Weight of layer wet}}{\text{Weight of layer dry}} = \text{Swelling factor}$$

The wet scratch strength was determined by passing a metal tip of specified size over the wet layer and loading it with a weight of increasing magnitude. The wet scratch strength is defined as the weight at which the tip leaves a visible scratch trace on the layer. The greater the weight, the higher the wet scratch strength.

Reticulation is assessed with a magnifying glass (8×) after swelling (10 minutes) in water at 22° C. Uneven hardening of the gelatine-containing layers due to the insolubility of the hardener in aqueous solution results in localised differences in the vertical and horizontal swelling and hence to an uneven surface (reticulation).

2. As interlayer, a gelatine layer 1 μm in thickness,
3. As middle layer, a green sensitive silver halide emulsion layer 4 μm in thickness containing, per kg of emulsion, 22 g of silver chloro bromide (77 mol % AgCl), 80 g of gelatine and 13 g of the magenta component corresponding to the following formula:

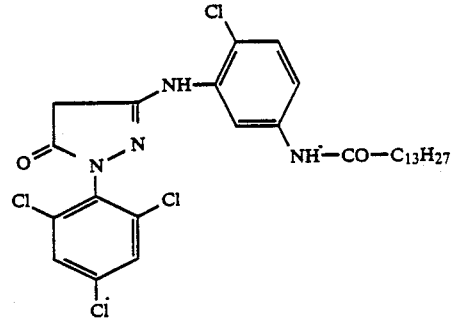

and 0.65 g of dibutyl naphthalene sulphonic acid

TABLE 1

| Sample Number | Hardener | Storage 36 hours at 57° C., 34% relative humidity | | | Storage 3 days at 23° C. with exclusion of moisture | Storage 7 days at 36° C. 80% relative humidity | | | Reticulation |
|---|---|---|---|---|---|---|---|---|---|
| | | Melting Point of the Layer (°C.) | Swelling Factor | Wet Scratch Strength (N) | Melting Point of the Layer (°C.) | Melting Point of the Layer (°C.) | Swelling Factor | Wet Scratch Strength (N) | |
| 1 | — | 40 | 6–8 | — | 40 | 40 | 6–8 | — | — |
| 2 | H-2 | 100 | 2.5 | 5.5 | 100 | 100 | 2.4 | 6.0 | — |
| 3 | H-3 | 100 | 3.1 | 4.5 | 100 | 100 | 2.9 | 4.7 | — |
| 4 | V-1 | 100 | 3.1 | <3.0 | 100 | 100 | 3.2 | 3.5 | Severe Reticulation |

No changes in the photographic properties of the samples such as sensitivity, fogging and gradation were observed in samples 1–3. Sample 4 showed severe reticulation and warping of the layers.

Table 1 shows that the compounds H2 and H3 according to the invention give rise to perfect layers which are homogeneously hardened whereas comparison compound V1 is not compatible with the anionic wetting agents in the layer and gives rise to reticulation due to coagulation.

EXAMPLE 2

A colour photographic material to be viewed by reflected light was prepared by successively applying the layers described below to a polyethylene-backed paper support coated with an adhesive layer. The emulsion layers contained the conventional wetting agents, stabilizers, etc.

1. The lowest layer cast was a blue sensitive silver halide emulsion layer 4 μm in thickness containing, per kg of emulsion, 25.4 g of silver chlorobromide (12 mol % AgCl), 80 g of gelatine, 0.9 g of dibutylnaphthalene sulphonic acid sodium and 34 g of the yellow component corresponding to the following formula

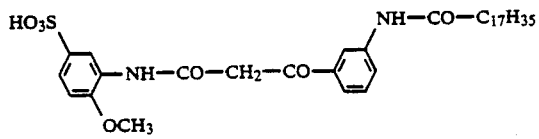

sodium,
4. An interlayer 1 μm in thickness as described under 2,
5. As top layer, a red sensitive silver halide emulsion layer 4 μm in thickness containing, per kg of emulsion, 23 g of silver chloro-bromide (80 mol % AgCl), 80 g of gelatine, 15.6 g of the cyan component corresponding to the following formula

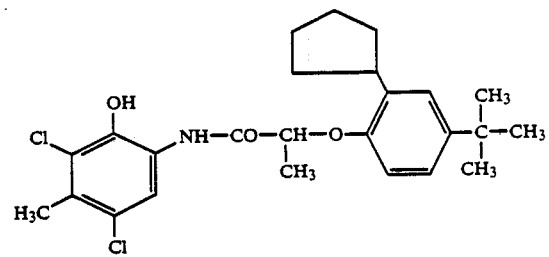

and 0.6 g of dibutylnaphthalene sulphonic acid sodium, and
6. a protective layer of gelatine 1 μm in thickness.

Aqueous solutions of the compounds H-2 and H-3 and of the hardener V-2 which was not according to the invention were applied to the dried layer packet (in each case 1/200 mol per 100 ml) and the layer packet was then dried. The layers were tested for crosslinking after storage under normal and tropical atmospheric conditions.

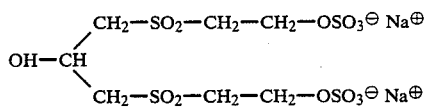

The results are shown in Table 2.

TABLE 2

| Sample Number | Hardener | Storage 36 hours at 57° C. 34% relative humidity | | | Storage 3 days at 23° C. with exclusion of moisture | Storage 7 days at 36° C. 80% relative humidity | | |
|---|---|---|---|---|---|---|---|---|
| | | Melting Point of the Layer (°C.) | Swelling Factor | Wet Scratch Strength (N) | Melting Point of the Layer (°C.) | Melting Point of the Layer (°C.) | Swelling Factor | Wet Scratch Strength (N) |
| 1 | H-2 | 100 | 3.8 | 4.5 | 100 | 100 | 3.5 | 5.0 |
| 2 | H-3 | 100 | 3.9 | 4.3 | 100 | 100 | 3.6 | 4.5 |
| 3 | V-2 | 40 | 5-6 | <2.0 | 40 | 100 | 4.2 | <2.0 |

Table 2 shows that the comparison substance V 2, hardens much more slowly than the hardeners according to the invention (high degree of after hardening).

When the compounds according to the invention are used, the whole layer packet was hardened sufficiently to be resistant to boiling after its storage under normal atmospheric conditions due to the diffusion of the compounds according to the invention into the layers. The layers have perfect interfaces and are free from reticulation.

Comparison compound V 2 does not undergo cross-linking until after the tropical storage. Severe after hardening therefore takes place during storage, with the result that the photographic properties change in the course of time (reduction in gradation, loss of maximum density).

When the hardeners according to the invention are used, the intensity of hardening does not diminish with increasing distance from the uppermost layer (layer with which the hardener is applied).

Photographic processing in conventional processing baths results in layers which have comparable photographic properties as regards sensitivity, fogging and gradation. In this form of application, the hardening system according to the invention is inert towards the emulsion, the colour couplers and the anionic wetting agents used.

EXAMPLE 3

A gelatine-containing AgBr/AgI emulsion suitably sensitized and stabilized with a protective layer 2 μm in thickness was applied to a cellulose acetate support. The layer packet was covered with a top casting of 1.5% by weight of gelatine containing 0.1% by weight of wetting agent corresponding to the formula

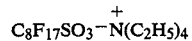

and hardener, this casting solution being applied in such a quantity that 0.08 mol of hardener acted on 1 kg of gelatine.

The layers were dried and stored 3 days at room temperature with exclusion of moisture and 3 days at 57° C. and 34% relative humidity.

The layer melting points, the swelling factor in water at 22° C. and the wet strength in the black and white developer at 38° C. were then determined.

V 1 and V 3 were used as comparison hardeners. V 3 corresponded to the following formula:

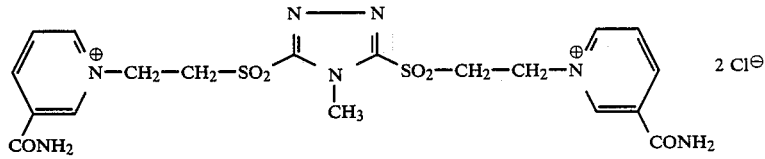

TABLE 3

| Compound 0.08 Mol/kg of Gelatine | Values after Storage for 3 days at 22° C. with exclusion of moisture | | | | Storage 3 days/57° C. 34% relative humidity | | |
|---|---|---|---|---|---|---|---|
| | Duration of resistance to boiling water (Min) | Swelling Factor | Wet Scratch Strength Black and White Developer 38° C. | Reticulation | Swelling Factor | Wet Scratch Strength Black and White Developer 38° C. | |
| V 1 | 7 | 3.0 | 2.0 | Severe Reticulation | 2.9 | 2.5 | |
| V 3 | 6 | 2.8 | 2.0 | " | 3.0 | 2.5 | |
| H 1 | 10 | 2.6 | 3.0 | No Reticulation | 2.7 | 5.0 | |

TABLE 3-continued

| Compound 0.08 Mol/kg of Gelatine | Values after Storage for 3 days at 22° C. with exclusion of moisture | | | | Storage 3 days/57° C. 34% relative humidity | | |
|---|---|---|---|---|---|---|---|
| | Duration of resistance to boiling water (Min) | Swelling Factor | Wet Scratch Strength Black and White Developer 38° C. | Reticulation | Swelling Factor | Wet Scratch Strength Black and White Developer 38° C. | |
| H 2 | 10 | 3.0 | 3.5 | " | 3.2 | 5.0 |
| H 3 | 10 | 4.4 | 1.0 | " | 3.9 | 2.5 |
| H 5 | 10 | 5.4 | 1.5 | " | 3.0 | 3.5 |

Table 3 shows that the compounds according to the invention do not give rise to any reticulation of the layer even when hardening is slightly weaker and that the hardening action is completely uniform in all layers in all cases. When the hardeners V 1 and V 3 not according to the invention aer used, the wetting agent (anionic) and the hardener separate after they have been mixed and a proportion of the hardener precipitates in the solution. The overall hardening effect is therefore uneven since the hardener, although readily water soluble, is fixed by the precipitation with the anionic wetting agent. It is no longer possible to harden the layers by covering them with a top layer of hardener, and reticulation occurs.

We claim:

1. Hardened binder layers in which the binder contains a protein, characterized in that they are hardened with a water soluble sulphate corresponding to the following formula

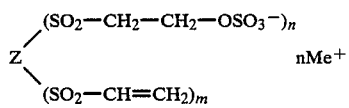

wherein
Me denotes a metal cation,
n represents an integer $>0$,
m represents an integer $\geq 0$,
m+n represents 2 and
Z corresponds to one of the following formulae:

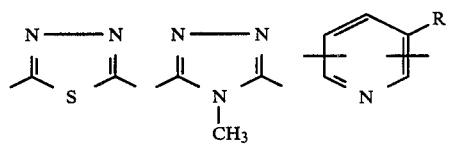

wherein R denotes $C_1$-$C_4$ alkyl, phenyl or $C_1$-$C_4$ alkoxy.

2. Hardened binder layers according to claim 1, characterized in that the protein is gelatine and contains anionic wetting agents.

3. Light sensitive photographic recording material containing at least one hardened gelatine layer, characterized in that a water soluble sulphate compound according to claim 1 was used for hardening.

4. Light sensitive photographic recording material according to claim 3, in which from 0.01 to 15% by weight of hardener, based on the dry weight of gelatine, was used and anionic wetting agents were used.

5. Light sensitive photographic recording material according to claim 3, in which from 0.1 to 5% by weight of hardener, based on the dry weight of gelatine, were used.

* * * * *